United States Patent
Ostrovsky et al.

(10) Patent No.: US 8,216,210 B2
(45) Date of Patent: *Jul. 10, 2012

(54) CONTROLLING MOVEMENT OF DISTAL PORTION OF MEDICAL DEVICE

(75) Inventors: Isaac Ostrovsky, Wellesley, MA (US); Jon T. McIntyre, Newtown, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/839,267

(22) Filed: Jul. 19, 2010

(65) Prior Publication Data

US 2011/0009700 A1  Jan. 13, 2011

Related U.S. Application Data

(63) Continuation of application No. 12/329,094, filed on Dec. 5, 2008, now Pat. No. 7,780,648.

(60) Provisional application No. 61/017,206, filed on Dec. 28, 2007.

(51) Int. Cl.
*A61M 25/00* (2006.01)
*A61M 31/00* (2006.01)
*B25G 1/10* (2006.01)

(52) U.S. Cl. .................... 604/528; 604/95.04; 16/430

(58) Field of Classification Search ............... 604/95.04, 604/528; 16/110.1–114.1, 405–430
See application file for complete search history.

(56) References Cited

U.S. PATENT DOCUMENTS

| | | | |
|---|---|---|---|
| 4,566,437 A | 1/1986 | Yamaguchi | |
| 4,617,915 A | 10/1986 | Arakawa | |
| 4,794,668 A * | 1/1989 | Lorence et al. | 16/110.1 |
| 4,998,916 A | 3/1991 | Hammerslag et al. | |
| 5,060,660 A | 10/1991 | Gambale et al. | |
| 5,125,130 A * | 6/1992 | Stanish | 16/430 |
| 5,230,154 A * | 7/1993 | Decker et al. | 30/276 |
| 5,281,214 A | 1/1994 | Wilkins et al. | |

(Continued)

FOREIGN PATENT DOCUMENTS

DE  26 03 370 A1  8/1977

(Continued)

OTHER PUBLICATIONS

International Search Report and Written Opinion for PCT/US09/48792, mailed Sep. 22, 2009; 15 pgs.

(Continued)

*Primary Examiner* — Victoria P Shumate
(74) *Attorney, Agent, or Firm* — Finnegan, Henderson, Farabow, Garrett & Dunner, LLP

(57) ABSTRACT

A medical device allows movement control of a distal end portion of the medical device and is adapted for one-handed operation. The medical device is capable of omni-directional control of the distal end portion of the device. The device has an elongated member including a deflectable portion at a distal end portion of the elongated member. The device also has a control portion disposed on the elongated member. This control portion can be a handle for one-handed use by an operator of the medical device. The control portion comprises an elastic element and a flexible element. Angular movement of a first portion of the control portion with respect to a second portion of the control portion results in amplification of that angular movement in the deflectable portion of the device.

18 Claims, 2 Drawing Sheets

U.S. PATENT DOCUMENTS

| | | | |
|---|---|---|---|
| 5,347,989 | A | 9/1994 | Monroe et al. |
| D351,652 | S | 10/1994 | Thompson et al. |
| 5,352,237 | A | 10/1994 | Rodak et al. |
| 5,397,304 | A * | 3/1995 | Truckai .................. 604/528 |
| 5,413,107 | A | 5/1995 | Oakley et al. |
| 5,611,777 | A | 3/1997 | Bowden et al. |
| 5,656,030 | A | 8/1997 | Hunjan et al. |
| 5,667,476 | A | 9/1997 | Frassica et al. |
| 5,702,349 | A | 12/1997 | Morizumi |
| 5,860,953 | A | 1/1999 | Snoke et al. |
| 5,882,333 | A | 3/1999 | Schaer et al. |
| 5,897,529 | A | 4/1999 | Ponzi |
| 5,906,590 | A | 5/1999 | Hunjan et al. |
| 5,957,865 | A | 9/1999 | Backman et al. |
| 6,007,531 | A | 12/1999 | Snoke et al. |
| 6,027,473 | A | 2/2000 | Ponzi |
| 6,059,739 | A | 5/2000 | Baumann |
| 6,066,125 | A | 5/2000 | Webster, Jr. |
| 6,123,699 | A | 9/2000 | Webster, Jr. |
| 6,171,277 | B1 | 1/2001 | Ponzi |
| 6,183,435 | B1 | 2/2001 | Bumbalough et al. |
| 6,183,463 | B1 | 2/2001 | Webster, Jr. |
| 6,198,974 | B1 | 3/2001 | Webster, Jr. |
| 6,203,507 | B1 | 3/2001 | Wadsworth et al. |
| 6,267,746 | B1 | 7/2001 | Bumbalough |
| 6,314,617 | B1 * | 11/2001 | Hastings .................. 16/436 |
| 6,468,260 | B1 | 10/2002 | Bumbalough et al. |
| 6,500,167 | B1 | 12/2002 | Webster, Jr. |
| 6,571,131 | B1 | 5/2003 | Nguyen |
| 6,605,086 | B2 | 8/2003 | Hayzelden et al. |
| 6,648,535 | B2 * | 11/2003 | Ferrara, Jr. .................. 401/6 |
| 6,679,873 | B2 | 1/2004 | Rabiner et al. |
| 6,783,510 | B1 | 8/2004 | Gibson et al. |
| 6,802,835 | B2 | 10/2004 | Rabiner et al. |
| 6,837,867 | B2 | 1/2005 | Kortelling |
| 6,945,956 | B2 | 9/2005 | Waldhauser et al. |
| 6,966,906 | B2 | 11/2005 | Brown |
| 6,968,599 | B2 | 11/2005 | Blauer et al. |
| 7,037,290 | B2 | 5/2006 | Gardeski et al. |
| 7,060,024 | B2 | 6/2006 | Long et al. |
| 7,060,025 | B2 | 6/2006 | Long et al. |
| 7,115,134 | B2 | 10/2006 | Chambers |
| 7,232,437 | B2 | 6/2007 | Berman et al. |
| 7,238,180 | B2 | 7/2007 | Mester et al. |
| 2004/0059191 | A1 | 3/2004 | Krupa et al. |
| 2004/0154133 | A1 * | 8/2004 | Polzin et al. .................. 16/430 |
| 2004/0193239 | A1 | 9/2004 | Falwell et al. |
| 2005/0080476 | A1 | 4/2005 | Gunderson et al. |
| 2005/0256375 | A1 | 11/2005 | Freed |
| 2005/0277874 | A1 | 12/2005 | Selkee |
| 2005/0277875 | A1 | 12/2005 | Selkee |
| 2005/0278897 | A1 * | 12/2005 | Tillim .................. 16/430 |
| 2005/0278898 | A1 * | 12/2005 | Tillim .................. 16/430 |
| 2005/0288627 | A1 | 12/2005 | Mogul |
| 2006/0142694 | A1 | 6/2006 | Bednarek et al. |
| 2006/0173448 | A1 | 8/2006 | Scheller et al. |
| 2006/0252993 | A1 | 11/2006 | Freed et al. |
| 2007/0156116 | A1 | 7/2007 | Gonzalez |
| 2007/0203474 | A1 | 8/2007 | Ryan et al. |
| 2007/0219529 | A1 | 9/2007 | Abe et al. |
| 2007/0270647 | A1 | 11/2007 | Nahen et al. |
| 2007/0282167 | A1 | 12/2007 | Barenboym et al. |
| 2008/0051802 | A1 | 2/2008 | Schostek et al. |

FOREIGN PATENT DOCUMENTS

| | | |
|---|---|---|
| EP | 0 521 595 B1 | 5/1999 |
| EP | 0 668 052 B1 | 1/2003 |
| WO | WO 93/20878 A | 10/1993 |
| WO | WO 2007/136829 A1 | 11/2007 |

OTHER PUBLICATIONS

International Search Report and Written Opinion for PCT/US09/34831, mailed May 13, 2009; 13 pgs.

International Search Report and Written Opinion for PCT/US08/86142, mailed Mar. 11, 2009; 10 pgs.

International Search Report and Written Opinion for PCT/US07/11912, mailed Sep. 12, 2008; 8 pgs.

International Search Report and Written Opinion for PCT/US09/49809, mailed Oct. 28, 2009; 10 pgs.

International Preliminary Report on Patentability for PCT/US07/11912, mailed Dec. 4, 2008; 6 pgs.

English language Derwent Abstract of DE 26 03 370 A1, published Aug. 25, 1977, Derwent Week 197735; 1 pg.

* cited by examiner

CONTROLLING MOVEMENT OF DISTAL PORTION OF MEDICAL DEVICE

CROSS-REFERENCE TO RELATED APPLICATIONS

This application is a continuation of application Ser. No. 12/329,094, filed Dec. 5, 2008, entitled "Controlling Movement of Distal Portion of Medical Device" of Isaac Ostrovsky et al., which claims priority to and the benefit of Provisional U.S. Patent Application Ser. No. 61/017,206, filed Dec. 28, 2007, the entirety of each of these applications is incorporated herein by reference.

TECHNICAL FIELD

The invention generally relates to medical devices with movable distal end portions. More specifically, the invention generally relates to a handle mechanism for controlling movement of a distal end portion of a medical device, such as a catheter or endoscope.

BACKGROUND INFORMATION

It is well established that there are major public health benefits from early detection and treatment of disease of internal organs such as the alimentary and excretory canals and airways, including the colon, esophagus, stomach, urethra, bladder, kidney, lungs, bronchi, uterus, heart, and other organ systems. Early detection of such diseases can be accomplished by periodic medical examinations aided by modern medical procedures and devices, such as catheters and endoscopes.

Some such procedures are performed with the aid of known steerable medical devices. Known steerable endoscopes and/or catheters are used in, for example, cardiovascular and electrophysiology applications. One known steerable catheter has an elongated catheter body with a distal tip portion that can be deflected into a semi-circle in one direction.

SUMMARY OF THE INVENTION

Precise deflection and articulation of a distal portion of a medical device can be important during a medical procedure in order to, for example, minimize friction force and trauma to any tissue at or near a targeted area within the body of a patient and/or to any tissue encountered as the distal portion of the medical device is moved toward the targeted area. A flexible control mechanism can be used to control the distal portion, and the flexible mechanism can be used to achieve omni-directional control and movement of the distal portion to access and/or survey the targeted area within the body of the patient. The medical device can have an elongated member with a deflectable tip at a distal end portion of the elongated member, and the medical device can have the flexible control mechanism formed integrally with or else coupled to the other (proximal) end of the elongated member. The flexible control mechanism can be a handle for one-handed use by an operator of the medical device. The handle can be used to controllably navigate the distal end portion of the device through the body of the patient to access and/or survey the targeted area within the body of the patient. In this manner, the device can improve the success of an examination or other medical procedure and can minimize pain, side effects, and risk as well as the need for sedation to the patient. Angular movement of the handle results in amplification of that angular movement in the deflectable tip of the device. Benefits of such a medical device include, but are not limited to, significant amplification of the movement of the handle to the deflectable tip of the elongated member with one-hand multidirectional control by a user or operator of the device. A slight deflection of the handle can be associated with a significant deflection of the deflectable tip of the elongated member.

In one aspect, the invention generally relates to a medical device that includes an elongated member and a control portion. The elongated member includes a deflectable portion at a distal end portion of the elongated member. The control portion of the device is disposed on the elongated member and includes an elastic element and a flexible element. Angular movement of a first portion of the control portion with respect to a second portion of the control portion is configured to amplify deflection of the deflectable portion of the elongated member.

Embodiments according to this aspect can include various features and/or one or more additional elements. For example, the control portion can be configured for angular movement in response to single-handed operation of the control portion by a user of the device. The control portion can be adapted to control 360 degree movement of the deflectable portion with respect to a longitudinal axis along which the device extends. The elastic element can define a plurality of lumens extending between a proximal end portion and a distal end portion, and each lumen of the plurality of lumens can be configured to receive a pull wire. The device can include a plurality of pull wires such that each pull wire of the plurality of pull wires corresponds to a respective lumen of the plurality of lumens of the elastic element. Each pull wire has an outer diameter that is less than an inner diameter of its respective lumen. The device can include first and second locking elements, with the first locking element disposed on the proximal end portion of the elastic element and attached to a proximal end portion of at least one pull wire of the plurality of pull wires, and with the second locking element disposed on the distal end portion of the elastic element and defining openings that correspond to lumens of the elastic element to allow the distal end portion of each of the pull wires to extend therethrough. At least one of the locking elements can be rigidly attached to the flexible element such that an angle is formed by the locking element and the flexible element and such that the angle is substantially constant despite angular movement of the control portion. Angular movement of the control portion by a user causes movement of at least one of the pull wires within its respective lumen. The elastic element can be made of one or more materials that make the elastic element easily compressed or stretched by the user, and the materials can include one or more of silicone, an elastomer, elastomeric polyurethane, polyether block amide (PEBA), ethylene-vinyl acetate (EVA), styrene-b-isobutylene-b-styrene (SIBS), an olefin elastomer, a styrenic block polymer, and a polyester elastomer, rubber, or the like, or any suitable combination thereof. The elastic element can include at least one longitudinally compressible spring. The flexible element can be configured to be substantially non-compressible, for example, in a longitudinal direction relative to the elastic element. The flexible element can include a mandrill or a tightly wound spring.

In another aspect, the invention generally relates to a handle mechanism for use with a deflectable medical device. The handle mechanism includes a control portion adapted for angular movement and configured to amplify deflection of a deflectable portion of the deflectable medical device in response to angular movement of the control portion. The control portion includes an elastic element that is compressible, and a flexible element that is received in a lumen defined by the elastic element and that is substantially non-compressible.

Embodiments according to this aspect can include various features and/or one or more additional elements. For example, the control portion can be configured for angular movement in response to single-handed operation of the control portion by a user of the device. The control portion can be adapted to control 360 degree movement of the deflectable portion of the deflectable medical device with respect to a longitudinal axis along which the deflectable medical device extends. The device can include a locking element that is fixedly coupled to each of the elastic element and the flexible element. The locking element can define an opening that is configured to receive at least a portion of a pull wire and that is configured to permit movement of the pull wire therethrough in response to the angular movement of the control portion.

BRIEF DESCRIPTION OF THE DRAWINGS

These and other features and advantages of the present invention will become better understood by reference to the following detailed description when considered in conjunction with the accompanying drawings, wherein.

DESCRIPTION

A medical device capable of omni-directional control includes an elongated member and a control portion disposed on the elongated member. At least a portion of the elongated member is adapted to be disposed in a body of a patient. The patient can be a human or other animal, for example. The elongated member includes a deflectable portion (e.g., a deflectable tip) at a distal end portion of the elongated member. The elongated member includes a proximal end portion and the distal end portion and defines a passage extending from the proximal end portion to the distal end portion. In some embodiments, the elongated member is flexible. The elongated member can be, for example, a catheter or an endoscope.

The control portion of the medical device is disposed on the elongated member. For example, in some embodiments, the control portion and the elongated member are separately manufactured and then coupled for use during a medical procedure. In another example, at least a portion of the control portion can be integrally formed with the elongated member. The control portion is configured for angular movement in response to operation of the medical device by a user (e.g., a physician or other medical personnel). In some embodiments, the control portion is configured to be operated by a single hand of the user. The control portion is adapted to control movement of the deflectable tip of the elongated member. In some embodiments, the control portion is adapted to control 360 degree movement of the deflectable tip with respect to a longitudinal axis along which the device extends. Angular movement of the control portion results in amplification of angular movement in the deflectable tip of the elongated member.

Figure 1:
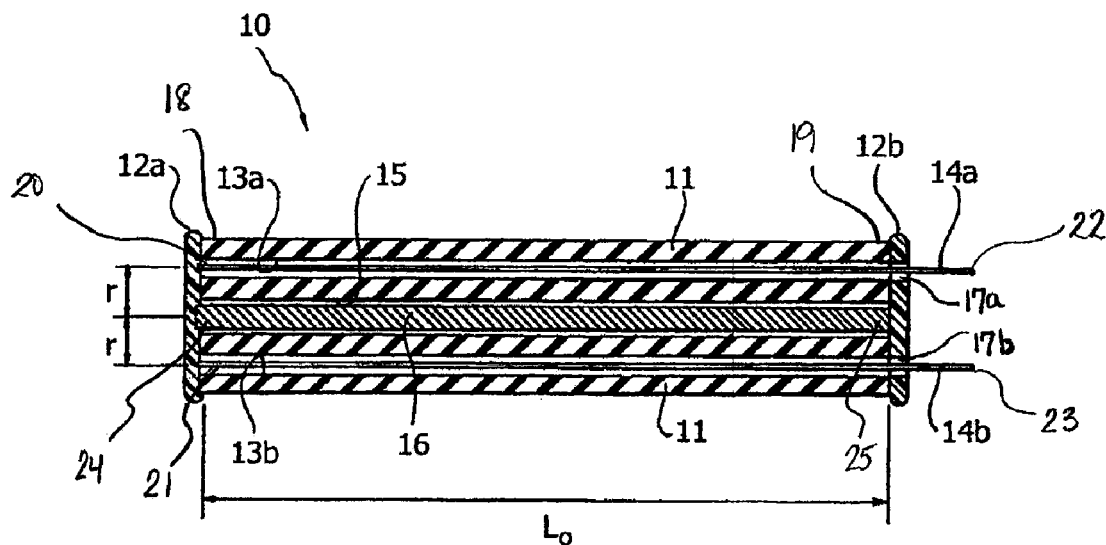
FIG. 1 depicts a longitudinal cross section of a control portion of a device in a neutral configuration in accordance with an embodiment.
Figure 2:
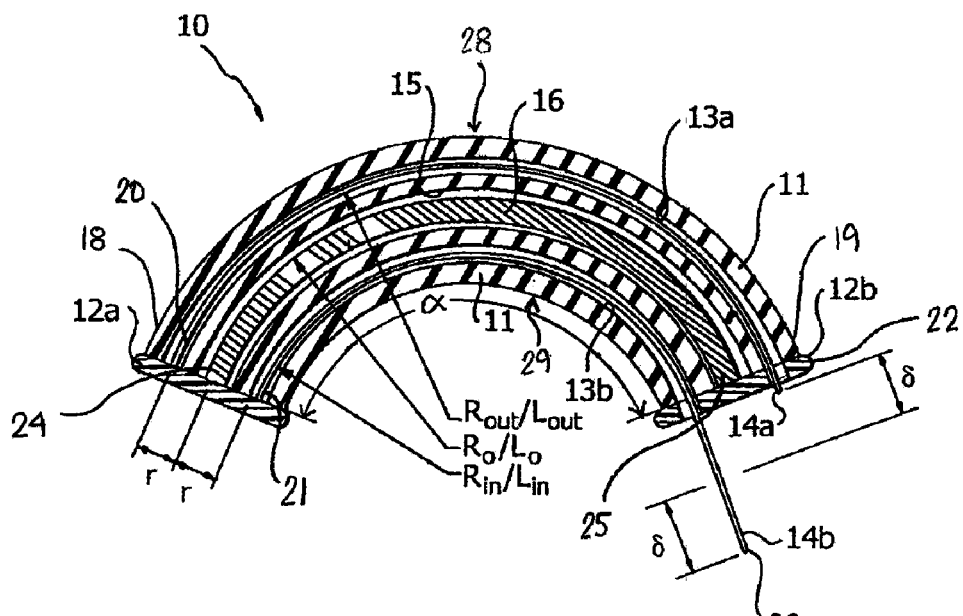
FIG. 2 depicts the longitudinal cross section of the control portion of the device of FIG. 1 in a tensile configuration in accordance with an embodiment.

A longitudinal cross-section of a control portion 10 of a medical device (shown in FIG. 3) according to an embodiment is depicted in FIGS. 1 and 2 in a first (or neutral) configuration and a second (or tensile or bent) configuration, respectively. The control portion 10 includes an elastic element 11 and a flexible element 16. The elastic element 11 includes a proximal end portion 18 and a distal end portion 19. The elastic element 11 defines a lumen 15 that extends from the proximal end portion 18 to the distal end portion 19 and that is configured to receive at least a portion of the flexible element 16. The elastic element 11 also defines a plurality of lumens 13a, 13b, each of which is configured to receive (or contain) at least a portion of a corresponding pull wire 14a, 14b, respectively. The diameter of each lumen 13a, 13b is greater than the diameter of the corresponding pull wire 14a, 14b received therein. In this manner, the pull wire 14a, 14b is freely slidable within its corresponding lumen 13a, 13b. The elastic element 11 can have a longitudinal configuration of any suitable cross-section, including, for example, a cylindrical cross-section. The elastic element 11 can be, for example, a cylindrical rod having a longitudinal (or center) axis of length $L_o$, as illustrated in FIG. 1.

The elastic element 11 is adapted to elastically (i.e., non-permanently) deform in response to an applied force. For example, in some embodiments, the elastic element 11 is adapted to deform in response to a force (or stress) applied by a hand of a user. When the application of force ceases, the elastic element 11 can return to its initial physical form (e.g., the elastic element 11 can return to the length, width, volume, shape, or the like, that the elastic element 11 exhibited prior to application of the force). In some embodiments, the elastic element 11 is adapted to be easily compressed, such as in response to exertion of a force upon a portion of the elastic element 11 by a hand of a user. Compression can be characterized as a reduction of a physical characteristic, (e.g., length, width, volume, or the like) of a material or object in response to a compressive stress. In some embodiments, for example, the elastic element 11 is adapted to exhibit a more than a minimal reduction in a certain physical characteristic in response to a compressive stress. For example, the elastic element 11 can be adapted to be compressed between about 2% and about 60% of its initial length (or width, volume, etc.) when a compressive stress is applied to the elastic element. In other words, if the elastic element 11 has an initial length of about 10 cm, the elastic element 11 can be adapted to be compressed between about 0.2 cm and about 6 cm, such that the elastic element 11 is between about 9.8 cm and about 4 cm in length when the compressive stress is applied. In some embodiments, the elastic element 11 is adapted to be compressed to about 50% of its initial length. In other embodiments, the elastic element 11 is adapted to be compressed to less than 60% of its initial length. The elastic element 11 can be adapted to be easily stretched, such as in response to exertion of a force (or stress) upon a portion of the elastic element 11 by a hand of a user. For example, the elastic element 11 can be adapted to be stretched to have a length, width, and/or volume greater than a length, width, and/or volume, respectively, of the elastic element 11 prior to application of the stress. In some embodiments, for example, the elastic element 11 is adapted to be stretched to have a length that is between about 2% and about 50% greater than the length of the elastic element 11 prior to application of the stress. For example, if the elastic element 11 is about 10 cm in length, the elastic element 11 can be adapted to be stretched to a length that is between about 10.2 cm and about 15 cm. In other embodiments, the elastic element 11 can be adapted to stretch to a length that is greater than 150% of the initial length of the elastic element 11.

In some embodiments, the elastic element 11 is compressible and/or stretchable, at least in part, because the elastic element 11 is at least partially constructed of an elastic material. In some embodiments, for example, the elastic element 11 is at least partially constructed of silicone. In some embodiments, the elastic element 11 is at least partially constructed of a material that is or includes another elastomer including, but not limited to, elastomeric polyurethane, polyether block amide (PEBA), ethylene-vinyl acetate (EVA), styrene-b-isobutylene-b-styrene (SIBS), an olefin elastomer, a styrenic block polymer, a polyester elastomer, rubber, or the like, or any suitable combination thereof. In some embodiments, the elastic element 11 is compressible and/or stretchable because, at least in part, of a physical configuration (e.g., boundary conditions, size, shape, thickness) of the elastic element 11. For example, in some embodiments, the elastic element 11 includes or is in the form of at least one longitudinally compressible and/or stretchable spring.

The flexible element 16 of the control portion 10 has a proximal end portion 24 and a distal end portion 25. At least a portion of the flexible element 16 of the control portion 10 is received or housed within the lumen 15 of the elastic element 11. The flexible element 16 is adapted to be substantially non-compressible. In other words, the flexible element 16 is adapted to exhibit no or minimal physical compression in response to a compressive stress, such as a compressive stress applied by the hand of a user during a medical procedure. In some embodiments, for example, the flexible element 16 is adapted to be compressed by up to about 2% of the flexible element's 16 initial length, width, and/or volume. For example, if the flexible element 16 is about 10 cm in length, the flexible element 16 is adapted to be compressed up to about 0.2 cm, i.e., shortened to a length down to about 9.8 cm.

In some embodiments, the flexible element 16 is at least partially constructed of a substantially non-compressible material. For example, the flexible element 16 can be constructed of a metal or a plastic. In some embodiments, the flexible element 16 includes or is at least partially constructed of, for example, stainless steel and/or nitinol. As used herein, nitinol is a shape memory material that is or includes a nickel-titanium alloy. In some embodiments, the flexible element 16 is substantially non-compressible due, at least in part, to a physical characteristic (e.g., boundary condition, size, shape, thickness) of the flexible element 16. For example, the flexible element 16 can include or be configured as a mandrel or a tightly wound spring.

The flexible element 16, however, is capable of angular movement. In other words, a first portion of the flexible element 16 (e.g., the proximal end portion 24) is configured to be moved or bent with respect to a second portion of the flexible element 16 (e.g., the distal end portion 25) and/or with respect to an axis along which the flexible element 16 extends (e.g., the longitudinal axis). In this manner, the flexible element 16 can be characterized as a bendable mechanism. The flexible element 16 can have a length substantially similar to the length $L_o$ of the longitudinal axis of the control portion 10.

The control portion 10 includes locking elements 12a, 12b disposed on distinct portions of the control portion 10. As illustrated in FIGS. 1 and 2, in some embodiments, the locking element 12a is coupled to the proximal end portion 18 of the elastic element 11 and/or to the proximal end portion 24 of the flexible element 16. In some embodiments, the locking element 12b is coupled to the distal end portion 19 of the elastic element 11 and/or to the distal end portion 25 of the flexible element 16. In some embodiments, the flexible element 16 is rigidly attached to at least one of the locking elements 12a, 12b, for example, such that a 90-degree angle is formed between the longitudinal axis of the elastic element 11 and a surface of the at least one locking element 12a, 12b at the point of attachment. The locking elements 12a, 12b can be constructed of any suitable material. For example, in some embodiments, at least one of the locking elements 12a, 12b is constructed of or includes a rigid plastic or metal. At least one of the locking elements 12a, 12b can be molded to the elastic element 11.

Figure 3:
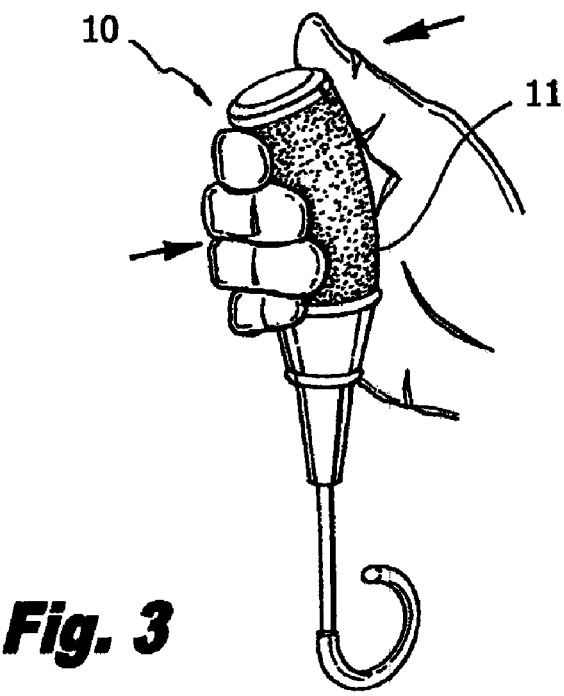
FIG. 3 depicts one-handed use by a user of a control portion of a device in accordance with an embodiment.

The locking element 12b defines openings 17a, 17b, which are in fluid communication with the lumens 13a, 13b, respectively, of the elastic element 11. A proximal end portion 20, 21 of each pull wire 14a, 14b, respectively, is attached to the locking element 12a. A distal end portion 22, 23 of each pull wire 14a, 14b is adapted to extend through the openings 17a, 17b, respectively, defined by the locking, element 12b. In this manner, each pull wire 14a, 14b can slide back and forth through the opening 17a, 17b, respectively, and within the corresponding lumen 13a, 13b, respectively, in response to the angular movement or bending of the control portion 10. The distal end portions 22, 23 of the pull wires 14a, 14b, can be coupled to a deflectable portion of the medical device. Thus, deflection of the deflectable portion can be controlled by controlling angular movement of the control unit 10, e.g., with a single hand of the user. Such angular movement or bending of the control unit 10 by a user is depicted in FIG. 3.

For purposes of explanation and example, FIGS. 1 and 2 depict the elastic element 11 as defining two lumens 13a, 13b and the control portion 10 as including two corresponding pull wires 14a, 14b. In other embodiments, however, a control portion can include any suitable number of lumens and/or pull wires; for example, in other embodiments, the control portion can include three, four, or more lumens and/or three, four, or more pull wires. Improvement in the 360° control capability can be achieved by increasing the number of pull wires. For example, three pull wires spaced 120° apart could be used.

Referring to FIG. 2, the control portion 10 is illustrated in its tensile configuration. The elastic element 11 and the flexible element 16 of the control portion 10 have a substantially equal bend angle α when the control portion 10 is in its tensile configuration. The elastic element 11, however, has a bend radius that is different than a bend radius of the flexible element 16 when the control portion 10 is in its tensile configuration. For example, as illustrated in FIG. 2, when the control portion is in its tensile configuration, the flexible element 16 has a bend radius of $R_o$, a first portion (or side) 29 of the elastic element 11 has a bend radius of $R_{in}$, and a second (or opposing) portion (or side) 28 of the elastic element 11 has a bend radius of $R_{out}$.

The length $L_o$ of the longitudinal axis of the control portion 10 remains substantially constant, even when the control portion 10 undergoes angular movement (e.g., is moved to its tensile configuration as depicted in FIG. 2). Because the flexible element 16 is substantially non-compressible, there is substantially no compression of the flexible element 16 in a longitudinal direction, e.g., relative to the elastic element 11, when the control portion 10 undergoes angular movement. In other words, the length $L_o$ of the flexible element 16 is substantially constant when the control portion 10 is in its neutral configuration and when the control portion 10 is in its tensile configuration. Thus, when a compressive force (e.g., the bending force) is applied to the control portion 10, a portion of the elastic element 11 is compressed with respect to the flexible element 16 and another portion (e.g., an opposing portion) of the elastic element 11 stretches or extends with respect to the flexible element 16, as illustrated in FIG. 2. Said another way, the circumferential length of the first portion 29 of the elastic element 11 is different than the circumferential length of the second portion 28 of the elastic element 11 when the control portion 10 is in its tensile configuration. For example, as illustrated in FIG. 2, when the control portion is in its tensile configuration, the first portion 29 of the elastic element 11 is compressed to have a circumferential length of $L_{in}$ and the second portion 28 of the elastic element 11 is stretched to have a circumferential length of $L_{out}$. The circumferential length of $L_{out}$ is greater than the circumferential length of $L_{in}$.

When the control portion 10 is in its tensile position, and the first portion 29 is compressed, the inner lumen 13b of the elastic element 11 is also compressed and has the length of $L_{in}$. The pull wire 14b received in the lumen 13b of the elastic element 11 does not compress when the control portion 10 is moved to its tensile configuration. Thus, the distal end portion 23 of the pull wire 14b is extended a certain length δ through the opening 17b of the elastic element 11 and out of the lumen 13b of the elastic element 11 of the control portion 10. The amount of the lumen 13b compression is equal to (or associated with) the pull wire 14b extension length δ.

The value of this compression and, correspondingly, the extension of the pull wire 14b that occurs when the control portion 10 is in its tensile position could be calculated as follows:

$$\delta = L_o - L_{in} = (2\Pi R_o - 2\Pi R_{in}) \times \alpha/2\Pi$$

In the above calculation, α is the amount of the bend angle in radians. As such, α/2Π is a portion of a circle (not shown) that could be completed from the angular bend in the control portion 10.

The relationship between the $R_{in}$ and $R_o$ can be described as $R_{in} = R_o - r$, where r is the amount of pull wire offset from the longitudinal axis of the elastic element 11. The formula for the extension δ of the pull wire 14b can be written as:

$$\delta = L_o - L_{in} = \{2\Pi R_o - 2\Pi(R_o - r)\} \times \alpha/2\Pi r = 2\Pi(R_o - R_o + r) \times \alpha/2\Pi = r \times \alpha$$

Thus, the pull wire extension δ is substantially equal to the amount of the bend angle α times the pull wire offset r from the longitudinal axis of the control portion 10:

$$\delta = r \times \alpha$$

Similarly, referring to FIG. 2, the amount of pull wire retracted inside the outer lumen 13a of the elastic element 11 when the control portion 10 in its tensile configuration is substantially equal to the amount of pull wire extension δ from the inner lumen 13b of the elastic element 11.

As illustrated in FIG. 2, when the pull wire 14a is moved or pulled in a proximal direction (e.g., via movement of locking mechanism 12a), the flexible element 16 is not compressed, and thus the first side 29 of the elastic element 11 compresses exposing the second pull wire 14b and the second side 28 of the elastic element 11 stretches or extends, thus retracting the first pull wire 14a into the lumen 13a of the elastic element 11. This results in angular movement, or bending, of the control portion 10. The bend angle α and the amount of the pull wire extension δ are calculable by the above formula.

For a given pull wire movement δ, the product of pull wire offset r times bend angle α remains constant. Thus, if the pull wire offset r is increased, the bend angle α would proportionally decrease. For example, for a soft plastic extrusion with a pull wire lumen offset of 1.25 mm (r=1.25 mm), the length of pull wire extension (or travel) δ inside the lumen would be:

$$90° (\alpha=\pi/2=1.57 \text{ radians}) \delta=1.25\times1.57=2 \text{ mm}$$

and similarly, $$180° (\alpha=\pi=3.14 \text{ radians}) \delta=1.25\times3.14=4 \text{ mm}$$

Thus, for a given bend angle α, the length of pull wire extension δ is directly proportional to the pull wire offset r. For example, in some embodiments, a pull wire offset of 12.5 mm (r=12.5 mm) results in a 10 times increase in pull wire extension than the 90° bend angle and 1.25 mm extrusion length example above, namely δ=20 mm.

Alternatively, in order to determine the deflection or bend angle, one can simply perform the inverse operation, namely:

$$\delta=2 \text{ mm } \alpha=\delta/r=2/12.5=0.16 \text{ radian}=9°$$

and similarly, $$\delta=4 \text{ mm } \alpha=\delta/r=4/12.5=0.32 \text{ radian}=18°$$

In this manner, the amount of angular movement sensitivity is determined by the configuration (or dimensions) of the control portion 10, and thus the control portion 10 can be adapted to cause amplified angular movement at the deflectable portion of the medical device. In other words, for example, the control portion 10 can be manufactured to having a specified pull wire offset r to achieve a desired amount of deflection of a distal end portion of the medical device in response to a specified degree of angular movement of the control portion 10.

Figure 4:
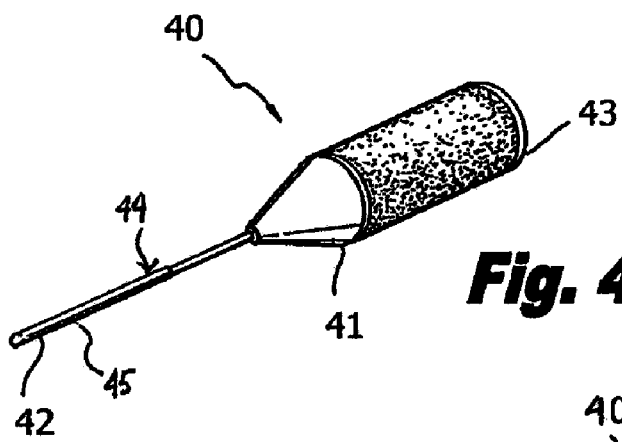
FIG. 4 depicts a schematic drawing of a device in accordance with an embodiment in a straight and neutral position.

FIG. 4 is a schematic drawing of a device 40 in a straight (or neutral) position. The device 40 includes a control portion 41 and an elongated member 44, and defines a distal end portion 42 and a proximal end portion 43. The control portion 41 is disposed on the proximal end portion 43 of the device 40. When the device 40 is in its straight (or neutral) position, each of the control portion 41 and the elongated member 44 is also in a neutral position. The distal end portion 42 of the elongated member 44 is adapted to be inserted into a body of a patient.

The elongated member 44 includes a deflectable portion 45 (or deflectable tip). The distal end portion 42 of the elongated member 44, and more particularly the deflectable portion 45, is adapted to be deflected in response to movement of the control portion 41. For example, the device 40 can include pull wires (not shown; e.g., pull wires similar in many respects to pull wires 14a, 14b, described above) that each have a proximal end portion coupled to the control portion 41 and a distal end portion coupled to the deflectable portion 45 of the elongated member. The pull wires are adapted to move in response to angular movement of the control portion 41, as described above with respect to FIGS. 1 and 2 and control portion 10. The deflectable portion 45 of the elongated member 44 is adapted to move in response to movement of the pull wires. Thus, the control portion 41 is adapted to control deflection of the deflectable portion 45 of the elongated member 44.

Figure 5:
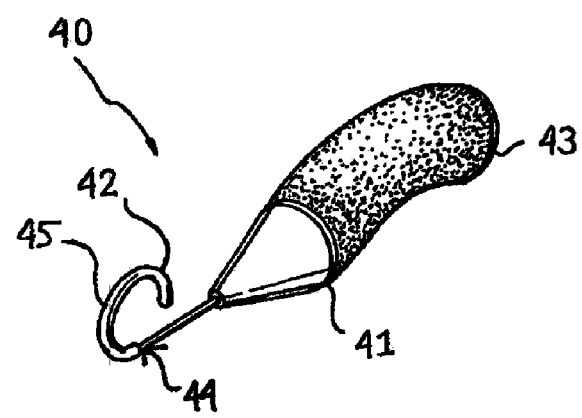
FIG. 5 depicts a schematic drawing of the device of FIG. 4 in a tensile position.

FIG. 5 is a schematic drawing of the device 40 in a tensile position. As illustrated in FIG. 5, the control portion 41 is angled or bent (e.g., by a user), and thus angular movement of a deflectable portion 45 at a distal end portion 42 of the device 40 is amplified.

Benefits of the present invention include providing for significant amplification of movement of the proximal control portion 10, 41, of the device with respect to movement of the distal deflectable portion of the device with one-hand multidirectional control by a user. Essentially, a slight deflection of the control portion (e.g., control portion 10, 41) on the proximal end portion (e.g., proximal end portion 43) produces a significant deflection of the distal tip (e.g., distal end portion 42 and/or deflectable portion 45) of the device, such as an endoscope or a catheter.

In some embodiments, various components of the devices described herein can be monolithically (or integrally) constructed. For example, in some embodiments, at least one of the locking elements 12a, 12b, can be monolithically constructed with the elastic element 11 or the flexible element 16. In another example, at least a portion of the control portion 41 can be monolithically constructed with at least a portion of the elongated member 44.

While various embodiments of the invention have been described above, it should be understood that they have been presented by way of example only, and not limitation.

What is claimed is:

1. A medical device, comprising:
    a handle configured to elastically deform in response to an applied force, the handle including a proximal end, a distal end, and a plurality of lumens extending therebetween, wherein the handle further includes an elongated flexible element disposed within the handle;
    at least one pull wire extending through at least one of the plurality of lumens; and
    an elongate member extending from the distal end of the handle, the elongate member including a deflectable distal region;
    wherein the handle is configured to move from a first neutral configuration to a second tensile configuration upon the application of the applied force so as to move at least one of a proximal end and a distal end of the flexible element relative to the other of the proximal and distal ends of the flexible element; and
    wherein the flexible element and the handle have substantially equal bend angles when the handle is in the second tensile configuration.

2. The medical device of claim 1, wherein the longitudinal length of the flexible element is substantially constant regardless of the configuration of the handle.

3. The medical device of claim 2, wherein the handle is configured such that a circumferential length of a first portion of the handle is different than a circumferential length of a second portion of the handle while the handle is in the second tensile configuration.

4. The medical device of claim 3, wherein the first portion of the handle is compressed relative to the flexible element, and the second portion of the handle is stretched relative to the flexible element, when the handle is moved from the first neutral configuration to the second tensile configuration.

5. The medical device of claim 1, wherein the flexible element has a different bend radius than the handle when the handle is in the second tensile configuration.

6. The medical device of claim 1, wherein the flexible element includes at least one of a mandrel and a spring.

7. The medical device of claim 1, wherein the handle is at least one of substantially compressible and stretchable in response to the applied force.

8. The medical device of claim 7, wherein the applied force is a force from a single hand of a user.

9. The medical device of claim 1, wherein the at least one pull wire includes a plurality of pull wires, each pull wire of the plurality of pull wires disposed within a respective lumen of the plurality of lumens; and
    wherein elastic deformation of the handle is configured to simultaneously displace at least one of the plurality of pull wires with respect to the corresponding lumen of the plurality of lumens a first distance, and displace at least another of the plurality of pull wires with respect to the corresponding lumen a second distance, the first distance and the second distance being substantially equivalent.

10. The medical device of claim 1, wherein movement of the handle is configured to deflect the deflectable distal region of the elongate member.

11. A medical device, comprising:
    a handle configured to elastically deform in response to an applied force, the handle including a proximal end, a distal end, and a plurality of lumens extending therebetween, wherein the handle further includes an elongated flexible element disposed within the handle;
    an elongate member extending from the distal end of the handle, the elongate member including a deflectable distal region;
    a plurality of pull wires, each pull wire of the plurality of pull wires corresponding to and extending through a respective lumen of the plurality of lumens of the handle;
    a first locking element disposed on the proximal end of the handle, the first locking element attached to a proximal end of at least one pull wire of the plurality of pull wires; and
    a second locking element disposed on the distal end of the handle and defining a plurality of openings, each opening of the plurality of openings aligned with a corresponding lumen of the plurality of lumens such that a distal end of each pull wire extends through the respective opening of the second locking element, at least a portion of each pull wire slidable within its respective lumen in response to the elastic deformation of the handle;
    wherein the handle is configured to move from a first neutral configuration to a second tensile configuration upon the application of the applied force so as to move at least one of a proximal end and a distal end of the flexible element relative to the other of the proximal and distal ends of the flexible element.

12. A method of operating a medical device, comprising:
    applying a force to an elastically deformable control portion of a medical device, the medical device including an elongated member having a deflectable region at a distal end of the elongated member, the control portion having a flexible element therein and defining a plurality of lumens extending between a proximal end and a distal end of the control portion, and at least one pull wire extending through at least one of the plurality of lumens, wherein the force causes the control portion to elastically deform and move from a first neutral configuration to a second tensile configuration so as to move at least one of a proximal end and a distal end of the flexible element relative to the other of the proximal and distal ends of the flexible element;
    wherein applying the force to the control portion further includes bending the control portion such that the flexible element and the control portion have a substantially equal bend angle when the control portion is in the second tensile configuration.

13. The method of claim 12, wherein the flexible element has a different bend radius than the control portion when the control portion is in the second tensile configuration.

14. The method of claim 13, wherein, after applying the force, the control portion is configured such that a circumferential length of a first portion of the control portion is different than a circumferential length of a second portion of the control portion.

15. The method of claim 12, wherein the first portion of the control portion is compressed relative to the flexible element and the second portion of the control portion is stretched relative to the flexible element.

16. The method of claim 12, wherein the at least one pull wire includes a plurality of pull wires, each pull wire of the plurality of pull wires disposed within a respective lumen of the plurality of lumens; and
    wherein applying force to the control portion simultaneously displaces at least one of the plurality of pull wires with respect to the corresponding lumen of the plurality of lumens a first distance, and displaces at least another of the plurality of pull wires with respect to the corresponding lumen a second distance, the first distance and the second distance being substantially equivalent.

17. The method of claim 12, wherein applying force to the control portion deflects the deflectable region of the elongated member.

18. The method of claim 12, wherein the control portion is at least one of substantially compressible and stretchable; and wherein a length of the flexible element is substantially constant regardless of the configuration of the control portion.

* * * * *